(12) United States Patent
Rao et al.

(10) Patent No.: US 9,233,967 B2
(45) Date of Patent: Jan. 12, 2016

(54) PROCESS FOR THE PREPARATION OF SITAGLIPTIN AND INTERMEDIATE COMPOUNDS

(71) Applicant: CIPLA LIMITED, Mumbai (IN)

(72) Inventors: Dharmaraj Ramachandra Rao, Thane (West) Maharashtra (IN); Rajendra Narayanrao Kankan, Mumbai Maharashtra (IN); Maruti Ghagare, Thane (West) Maharashtra (IN); Swati Atul Kadam, Thane Maharashtra (IN)

(73) Assignee: CIPLA Limited, Mumbai (IN)

( * ) Notice: Subject to any disclaimer, the term of this patent is extended or adjusted under 35 U.S.C. 154(b) by 0 days.

(21) Appl. No.: 14/419,980

(22) PCT Filed: Aug. 8, 2013

(86) PCT No.: PCT/GB2013/000338
§ 371 (c)(1),
(2) Date: Feb. 6, 2015

(87) PCT Pub. No.: WO2014/023930
PCT Pub. Date: Feb. 13, 2014

(65) Prior Publication Data
US 2015/0197523 A1    Jul. 16, 2015

(30) Foreign Application Priority Data

Aug. 8, 2012    (IN) .......................... 2278/MUM/2012

(51) Int. Cl.
*C07D 487/04*    (2006.01)
(52) U.S. Cl.
CPC .................................. *C07D 487/04* (2013.01)
(58) Field of Classification Search
USPC ....................................................... 544/350
See application file for complete search history.

(56) References Cited

U.S. PATENT DOCUMENTS 6,699,871 B2    3/2004 Edmondson et al.

FOREIGN PATENT DOCUMENTS

| WO | WO 2004087650 A2 | 10/2004 |
| WO | WO 2009064476 A1 | 5/2009 |
| WO | WO 2009084024 A2 | 7/2009 |
| WO | WO 2010122578 A2 | 10/2010 |
| WO | WO 2011049344 A2 | 4/2011 |
| WO | WO 2011102640 A2 | 8/2011 |
| WO | WO 2012025944 A2 | 3/2012 |
| WO | WO 2012042534 A2 | 4/2012 |

OTHER PUBLICATIONS

International Search Report and Written Opinion issued by the European Patent Office for International Application No. PCT/GB2013/00338 mailed Oct. 24, 2013, 14 pages.

Kim Dooseop et al: "( 2R)-4-Oxo-4-[3-(Tri fl uoromethyl )-5,6-d i hydro[1,2,4]triazolo[4,3-a]pyrazin-7(8H)-yl]-1-(2,4,5-trifluorophenyl)butan-2-amine: A Potent, Orally Active Dipeptidyl Peptidase IV Inhibitor for the Treatment of Type 2 Diabetes", Journal of Medicinal Chemistry, American Chemical Society, vol. 48, Jan. 1, 2005, pp. 141-151.

Hansen Karl B et al: "First Generation Process for the Preparation of the OPP-IV Inhibitor Sitagliptin", Organic Process Research and Development, American Chemical Society, US, vol . 9, No. 5, Sep. 1, 2005, pp. 634-639.

Pingwah Tang: "Discussion Addendum for: Boric Acid Catalyzed Amide Formation from Carboxylic Acids and Amines: n-Benzyl-4-phenylbutyramide", Organic Synthesis, vol. 89, Apr. 16, 2012, pp. 432-437.

Vijaya R. Pattabiraman et al: "Rethinking amide bond synthesis", Nature, vol. 480, No. 7378, Dec. 21, 2011, pp. 471-479.

*Primary Examiner* — Kristin Vajda
(74) *Attorney, Agent, or Firm* — Haynes and Boone, LLP

(57) ABSTRACT

There is provided a process for the preparation of sitagliptin or a pharmaceutically acceptable salt thereof, and a process for the preparation of intermediate compounds useful in the preparation of sitagliptin. In particular, there is provided a process comprising condensing 3-tert-butoxycarbonylamino-4-(2,4,5-trifluorophenyl)butyric acid of formula (II) with 3-(trifluoromethyl)-5,6,7,8-tetrahydro-[1,2,4]triazolo[4,3-a]pyrazine of formula (III) or a salt thereof in presence of a catalyst to obtain (R)-tert-butyl-4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV) or a pharmaceutically acceptable salt thereof. The catalyst is represented by the compound of formula (V). Compound of formula (IV) or its pharmaceutically acceptable salt obtained may be deprotected to obtain a compound of formula (I).

25 Claims, No Drawings

PROCESS FOR THE PREPARATION OF SITAGLIPTIN AND INTERMEDIATE COMPOUNDS

This application is a U.S. National Stage patent application of Patent Cooperation Treaty Application No. PCT/GB2013/000338 filed Aug. 8, 2013, which claims priority to Indian Application No. 2278/MUM/2012 filed Aug. 8, 2012, the disclosure of which is incorporated herein by reference in their entirety.

TECHNICAL FIELD OF THE INVENTION

The present invention relates to an improved process for the preparation of sitagliptin or a pharmaceutically acceptable salt thereof. The present invention also relates to a process for the preparation of an intermediate compound of formula (IV) or a pharmaceutically acceptable salt thereof.

BACKGROUND OF THE INVENTION

Sitagliptin is chemically known as 7-[(3R)-3-amino-1-oxo-4-(2,4,5-trifluorophenyl)butyl]-5,6,7,8-tetrahydro-3-(trifluoromethyl)-1,2,4-triazolo[4,3-a]pyrazine and represented as follows:

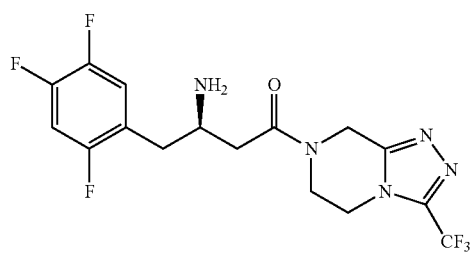

(I)

U.S. Pat. No. 6,699,871 discloses sitagliptin and describes the preparation of sitagliptin hydrochloride salt, while U.S. Pat. No. 7,326,708 claims the phosphate salt of sitagliptin or a hydrate thereof.

The key step in the synthesis of sitagliptin is the condensation of amino acid derivative with triazolo pyrazine compound. This being a peptide bond formation, according to the prior art, standard peptide coupling conditions and reagents are used.

Various patent applications such as WO2004087650, WO2009064476, WO2009084024, WO2010122578, WO2011102640, WO2011049344, WO2012025944 and WO2012042534, including U.S. Pat. No. 6,699,871, describe different methods of preparing sitagliptin and its pharmaceutically acceptable salts. However, all these applications describe the use of a standard peptide coupling agent with or without additive and in the presence or absence of a base for the condensation of the amino acid derivative with the triazolo pyrazine compound.

The common coupling reagents used are dicyclohexyl carbodiimide (DCC), 1-ethyl-3-(3'-dimethylaminopropyl) carbodiimide (EDC), diisopropyl carbodiimide (DIC), 1,1'-carbonyldiimidazole (CDI), carbonyldithiazole, 1-(3-dimethylaminopropyl)-3-ethylcarbodiimide methiodide, 1-tert-butyl-3-ethylcarbodiimide etc.

The common additives used are 1-hydroxy benzotriazole (HOBt), 1-hydroxy-7-azabenzotriazole (HOAt), 1-hydroxysuccinimide etc.

These reagents are used widely in the synthesis of various products as they are cost effective and readily available.

However, these reagents do have certain disadvantages, such as:

1) the reaction is exothermic;

2) use of basic catalyst;

3) competitive hydrolysis of activated carboxyl group;

4) removal of dicyclohexyl urea byproduct obtained in DCC-HOBt mediated reaction;

5) the hazardous nature of the reagents such as HOBt;

6) the by-products of the reactions are toxic and hazardous in nature.

Further, the transportation and subsequent storage and use are critical issues for the reagents containing the imidazole ring benzotriazoles, e.g. HOBt, and for reagents with an extra nitrogen in the phenyl ring, e.g. HOAt. Recent studies have found that these compounds are unstable with relatively high sensitivity to friction, spark, and electrostatic discharge resulting in burning or explosion.

Carboxydiimides, for example, are well known for their skin irritating properties. In addition, prolonged use of benzotriazole based coupling reagents and additives (e.g. HOBt, HBTU, or TBTU) may not only cause skin irritation and contact dermatitis, but also sensitization and allergic reaction of the respiratory tract. In industry, these disadvantages are even more significant.

Thus the use of these reagents has been found to be incompatible and non-eco-friendly at industrial scale. Thus, there is a need to develop an industrially feasible, less hazardous and more eco-friendly process, which at the same time provides improved yield and chemical purity, as well as improved optical purity. The present invention therefore seeks to address these issues.

SUMMARY OF THE INVENTION

According to the first aspect of the present invention, there is provided an improved process for the preparation of sitagliptin or a pharmaceutically acceptable salt thereof.

The process involves the step of condensing 3-tert-butoxycarbonylamino-4-(2,4,5-trifluorophenyl)butyric acid of formula (II)

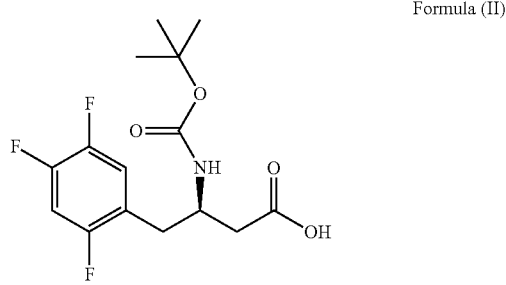 [SMILES: CC(C)(C)OC(=O)N[C@@H](CC(=O)O)Cc1cc(F)c(F)cc1F]

Formula (II)

with 3-(trifluoromethyl)-5,6,7,8-tetrahydro-[1,2,4]triazolo[4,3-a]pyrazine of formula (III) or a salt thereof

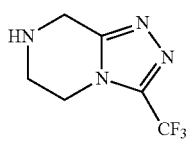

Formula (III)

in a suitable solvent in presence of a catalyst to obtain (R)-tert-butyl-4-oxo-4-(3-(trifluoromethyl)-5,6-dihydro-[1,2,4]-triazolo[4,3-a]pyrazin-7(8H)-yl)-1-(2,4,5-trifluorophenyl) butan-2-yl-carbamate of formula (IV) or a pharmaceutically acceptable salt thereof.

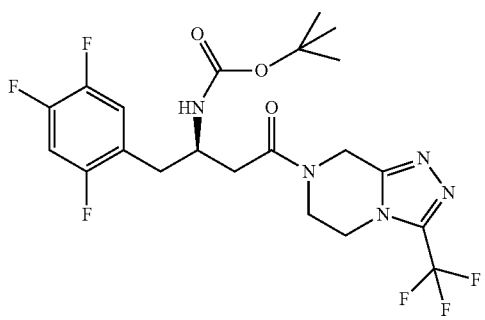

Formula (IV)

The compound of formula (IV) or a pharmaceutically acceptable salt thereof is then deprotected to obtain sitagliptin which then may be converted to its pharmaceutically acceptable salt.

According to another aspect of the invention there is provided a process for the preparation of a compound of formula (IV)

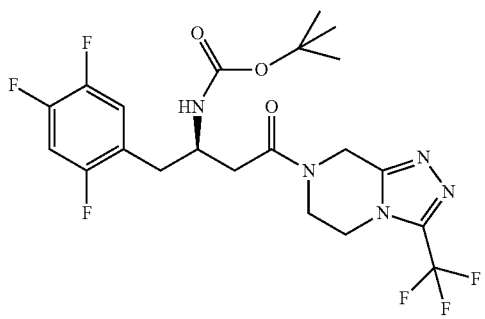

Formula (IV)

which process comprises:

a) condensing 3-tert-butoxycarbonylamino-4-(2,4,5-trifluorophenyl)butyric acid of formula (II)

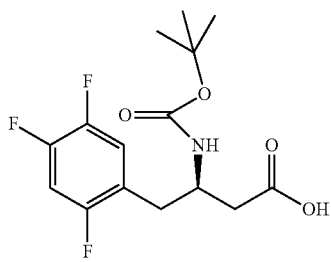

Formula (II)

with 3-(trifluoromethyl)-5,6,7,8-tetrahydro-[1,2,4]triazolo [4,3-a]pyrazine of formula (III) or a salt thereof

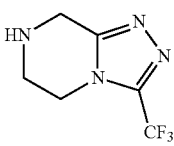

Formula (III)

in presence of a catalyst to obtain (R)-tert-butyl-4-oxo-4-(3-(trifluoromethyl)-5,6-dihydro-[1,2,4]-triazolo[4,3-a] pyrazin-7(8H)-yl)-1-(2,4,5-trifluorophenyl)butan-2-yl-carbamate of formula (IV) or a pharmaceutically acceptable salt thereof;
wherein the catalyst is represented by the compound of formula (V)

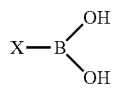

(V)

wherein X is independently selected from hydroxy, straight chain or branched chain $C_{1-5}$ alkyl optionally substituted with one or more groups, $C_{6-13}$ aryl optionally substituted with one or more groups, and an optionally substituted heterocyclic ring having one to four heteroatoms selected from oxygen, sulfur and nitrogen. The $C_{6-13}$ aryl group may be non-aromatic or aromatic.

The $C_{1-5}$ alkyl may be methyl, ethyl, n-propyl, isopropyl, n-butyl, sec-butyl, isobutyl or tert-butyl. The $C_{1-5}$ alkyl may also be substituted with one or more substituents, and when the $C_{1-5}$ alkyl is substituted, the substituent may be selected from the group consisting of halogen, nitro, $C_{1-9}$ alkyl, $C_{1-9}$ alkenyl, and $C_{1-9}$ alkoxy. Where the $C_{1-5}$ alkyl is substituted by halogen, the halogen may be selected from the group consisting of fluorine, chlorine, bromine and iodine.

The aryl group may be substituted by one or more substituents selected from the group consisting of halogen, nitro, $C_{1-9}$ alkyl, $C_{1-9}$ alkenyl, and $C_{1-9}$ alkoxy. Where the aryl group is substituted by halogen, the halogen may be selected from the group consisting of fluorine, chlorine, bromine and iodine. Preferably the halogen is a chlorine or bromine. The $C_{1-9}$ alkyl may be methyl, ethyl, n-propyl, isopropyl, n-butyl, sec-butyl, isobutyl or tert-butyl. The $C_{1-9}$ alkenyl group may be ethenyl, 2-propenyl, 1-propenyl, 1-butenyl, 2-butenyl or 3-butenyl. $C_{1-9}$ alkoxy means $C_{1-9}$ alkyl-oxy, and the $C_{1-9}$ alkyl of the $C_{1-9}$ alkoxy may be methyl, ethyl, n-propyl, isopropyl, n-butyl, sec-butyl, isobutyl or tert-butyl.

When X is an aryl group, the aryl group is preferably phenyl. The phenyl group may be substituted with one or more substituents as defined above. Preferably the phenyl group is substituted by one substituent, and more preferably the phenyl group is substituted by a halogen selected from chloro or bromo.

X may be a heterocyclic ring substituted with one or more substituents selected from the group consisting of halogen, nitro, $C_{1-9}$ alkyl, $C_{1-9}$ alkenyl, and $C_{1-9}$ alkoxy. The halogen may be selected from the group consisting of fluorine, chlorine, bromine and iodine. Preferably the halogen is a chlorine or bromine. The $C_{1-9}$ alkyl may be methyl, ethyl, n-propyl, isopropyl, n-butyl, sec-butyl, isobutyl or tert-butyl. The alkenyl group may be ethenyl, 2-propenyl, 1-propenyl, 1-butenyl, 2-butenyl or 3-butenyl. $C_{1-9}$ alkoxy means $C_{1-9}$ alkyl-oxy, and the $C_{1-9}$ alkyl of the $C_{1-9}$ alkoxy may be methyl, ethyl, n-propyl, isopropyl, n-butyl, sec-butyl, isobutyl or tert-butyl.

The heterocyclic ring substituent may be selected from the group consisting of furan, tetrahydrofuran, thiophene, pyrrole, pyrrolidine, pyran, pyridine, piperidine, imidazole, thiazole, dioxane, or pyrimidine. These heterocyclic ring substituents may be optionally substituted as defined above.

The process may further comprise b) deprotecting the compound of formula (IV) or its pharmaceutically acceptable salt obtained in step a) to obtain a compound of formula (I).

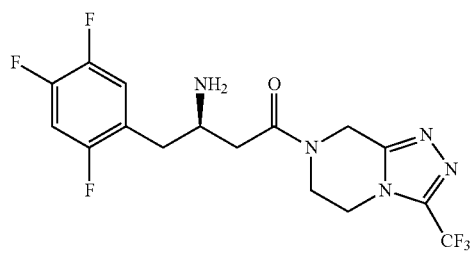

(I)

The deprotection may be by hydrogenation or acid hydrolysis. If the deprotection step is carried out by hydrogenation, this hydrogenation may be carried out using palladium on carbon or sodium borohydride.

The compound of formula (IV) may be isolated prior to the deprotection step (b). Alternatively, the compound of formula (IV) may be deprotected to obtain compound of formula (I) in situ without isolation of compound of formula (IV).

The term "in situ" is defined herein to mean within the reaction mixture and without isolation of the intermediate compound.

The process may further comprise converting the compound of formula (I) obtained in step b) to a pharmaceutically acceptable salt, and the compound of formula (I) may be isolated and purified prior being converted to a pharmaceutically acceptable salt. Alternatively, the compound of formula (I) may converted to a pharmaceutically acceptable salt in situ. Preferably, the pharmaceutically acceptable salt is the phosphate salt.

Preferably, the catalyst is selected from the group consisting of phenyl boronic acid, 2-halophenyl boronic acid, 3-halophenylboronic acid, and 4-halophenylboronic acid. The term "halo" may be defined as a fluorine, chlorine, bromine or iodine group. Preferably the halo group is a chlorine or bromine group. More preferably, the catalyst is selected from the group consisting of 2-chlorophenyl boronic acid, 3-chlorophenyl boronic acid, 4-chlorophenyl boronic acid, 2-bromophenyl boronic acid, 3-bromophenyl boronic acid, and 4-bromophenyl boronic acid. In further preferred embodiment, the catalyst is phenyl boronic acid.

The amount of catalyst used may be in the range of from 0.05 to 1.5 moles with respect to 1 mole of 3-tert-butoxycarbonylamino-4-(2,4,5-trifluorophenyl)butyric acid of formula (II).

The solvent used for the reaction may be selected from the group consisting of toluene, xylene, mesitylene, anisole, heptane, hexane, dimethyl formamide (DMF), dimethyl sulfoxide (DMSO), N-methyl pyrrolidone (NMP), dimethyl acetamide (DMA), N,N-diisopropyl ethylamine and ionic liquids.

Preferably the 3-(trifluoromethyl)-5,6,7,8-tetrahydro-[1,2,4]triazolo[4,3-a]pyrazine of formula (III) is in the form of a salt, preferably the hydrobromide salt or the hydrochloride salt.

When the 3-(trifluoromethyl)-5,6,7,8-tetrahydro-[1,2,4]triazolo[4,3-a]pyrazine of formula (III) is in the form of a salt, the reaction is preferably carried out in presence of a base, preferably an inorganic base or an organic base. When the base is an inorganic base, the base may be selected from the group consisting of sodium hydroxide, potassium hydroxide, lithium hydroxide, cesium hydroxide, sodium carbonate, sodium bicarbonate, potassium carbonate, potassium bicarbonate, lithium carbonate, and cesium carbonate. When the base is an organic base, the base may be selected from the group consisting of N,N-diisopropyl ethylamine, N,N-diisopropyl methylamine, triethyl amine, tert-butyl amine, 1-naphthyl amine, aniline, dimethyl aniline, piperidine, pyridine, imidazole, and lutidine. More preferably the base is N,N-diisopropyl ethylamine or triethyl amine.

In a further aspect of the invention there is provided a compound of formula (IV) or a pharmaceutically acceptable salt thereof when prepared by the process as described herein.

In a further aspect of the invention there is provided a compound of formula (I) or a pharmaceutically acceptable salt thereof when prepared by the process as described herein.

In a further aspect of the invention there is provided a pharmaceutical composition comprising a compound of formula (I) or a pharmaceutically acceptable salt thereof when prepared by the process as described herein, together with one or more pharmaceutically acceptable excipients. The pharmaceutical compositions of this aspect of the invention may be prepared according to methods known in the art. The suitable pharmaceutically acceptable excipients for inclusion in such pharmaceutical compositions would be known to those skilled in the art.

In a further aspect of the invention there is provided a compound of formula (I) or a pharmaceutically acceptable salt thereof when prepared by the process as described herein for use in medical treatment.

In a further aspect of the invention there is provided a compound of formula (I) or a pharmaceutically acceptable salt thereof when prepared by the process as described herein for use in inhibiting dipetidyl peptidase-IV enzyme activity in a patient in need thereof.

In a further aspect of the invention there is provided the use of compound of formula (I) or a pharmaceutically acceptable salt thereof when prepared by the process as described herein in the manufacture of a medicament for use in inhibiting dipetidyl peptidase-IV enzyme activity in a patient in need thereof.

In a further aspect of the invention there is provided a method of inhibiting dipetidyl peptidase-IV enzyme activity in a patient in need thereof comprising administering a compound of formula (I) or a pharmaceutically acceptable salt thereof when prepared by the process as described herein to the patient.

In a further aspect of the invention there is provided a compound of formula (I) or a pharmaceutically acceptable salt thereof when prepared by the process as described herein for use in the treatment of a disease selected from the group consisting of diabetes, obesity and high blood pressure. Preferably the disease is type 2 diabetes.

In a further aspect of the invention there is provided the use of compound of formula (I) or a pharmaceutically acceptable salt thereof when prepared by the process as described herein in the manufacture of a medicament for the treatment a disease selected from the group consisting of diabetes, obesity and high blood pressure. Preferably the disease is type 2 diabetes.

In a further aspect of the invention there is provided a method of treating a disease selected from the group consisting of diabetes, obesity and high blood pressure comprising administering a compound of formula (I) or a pharmaceutically acceptable salt thereof when prepared by the process as described herein to a patient. Preferably the disease is type 2 diabetes.

DETAILED DESCRIPTION OF THE INVENTION

The present invention relates to a process for the preparation of sitagliptin or a pharmaceutically acceptable salt thereof, and useful intermediate compounds in the preparation thereof.

The process comprises condensing 3-tert-butoxycarbonylamino-4-(2,4,5-trifluorophenyl) butyric acid of formula (II)

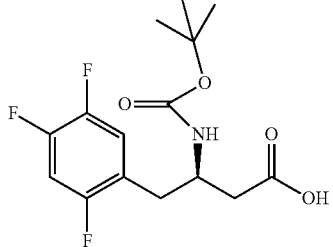

Formula (II)

with 3-(trifluoromethyl)-5,6,7,8-tetrahydro-[1,2,4]triazolo[4,3-a]pyrazine formula (III) or a salt thereof

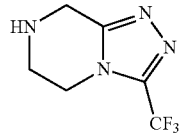

Formula (III)

in a suitable solvent and in presence of a catalyst to obtain (R)-tert-butyl-4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV) or a pharmaceutically acceptable salt thereof.

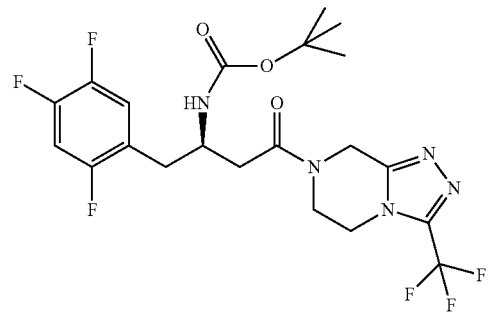

Formula (IV)

The catalyst is represented by the compound of formula (V)

(V)

Where X is independently selected from hydroxy, optionally substituted $C_{1-5}$ alkyl which may be straight chained or branched, non-aromatic or aromatic $C_{6-13}$ aryl which may be optionally substituted with one or more groups, and a heterocyclic ring having one to four heteroatoms selected from oxygen, sulfur and nitrogen which may be optionally substituted. The groups with which the aryl may be substituted may be selected from the group consisting of halogen, nitro, $C_{1-9}$ alkyl, $C_{1-9}$ alkenyl, and $C_{1-9}$ alkoxy. The heterocyclic ring may be optionally substituted with one or more substituents selected from the group consisting of halogen, nitro, $C_{1-9}$ alkyl, $C_{1-9}$ alkenyl, and $C_{1-9}$ alkoxy.

The catalyst may preferably be selected from the group comprising of phenyl boronic acid, 2-halophenyl boronic acid, 3-halophenyl boronic acid, 4-halophenyl boronic acid such as 2-chlorophenyl boronic acid, 3-chlorophenyl boronic acid, 4-chlorophenyl boronic acid, 2-bromophenyl boronic acid, 3-bromophenyl boronic acid, 4-bromophenyl boronic acid and the like.

The catalyst, which is boric acid or a boronic acid derivative, takes the role of a coupling reagent in generating an active ester suitable for amidation in a waste-free catalytic manner.

Amidation catalyzed by boric acid or a boronic acid derivative, such as phenyl boronic acid or 2-halophenylboronic acid, does not create any waste, giving water as the only by-product and the amide product can be isolated using just simple acid-base extraction.

The boric acid or boronic acid derivative of formula (V) reacts with 3-tert-butoxycarbonylamino-4-(2,4,5-trifluorophenyl)butyric acid of formula (II) to form monoacyloxy boronic acid intermediate of formula (VII) in solvent under reflux with the removal of water.

Upon reaction with an amine of formula (III), this intermediate of formula (VII) forms the desired carboxamide, i.e. compound of formula (IV), and regenerates back the catalytically active boric acid or boronic acid derivative of formula (V).

The mechanism of the reaction may be shown as follows:

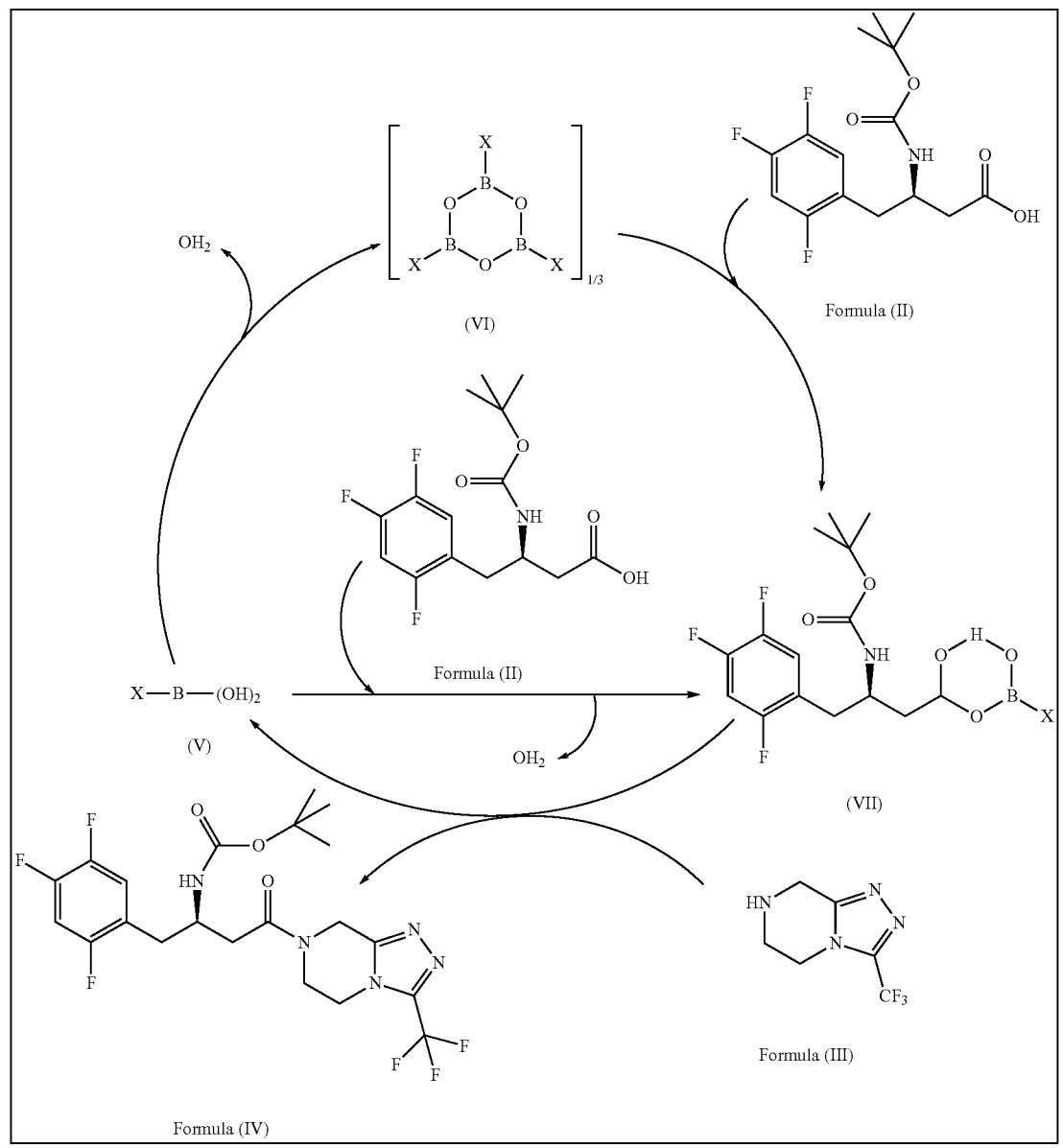

The advantages of using the boric acid or boronic acid derivative as a catalyst are as follows:
1) In most cases, no more than 5 mol % of the catalyst is required to catalyze the amidation. In all cases, the reactions proceed cleanly in high yields to the expected carboxamides.
2) No, or little, side reactions either with the unprotected amine group present in the amines or arylamines, or with the unprotected hydroxyl group present in the carboxylic acids, are observed.
3) The catalyst employed in the reactions, boric acid or a boronic acid derivative, is inexpensive and commercially available. The catalyst is a "green" catalyst, so it is environmentally friendly. By virtue of the simplicity of the process, the operation is easy to conduct. Therefore, it is amenable for large-scale preparations.
4) The catalytic amidation is an atom-economical process because it maximizes the incorporation of all materials used in the process into the final product. Therefore, it allows organic molecule architects for the quick building of molecular complexity.
5) Boronic acid derivatives or boric acid act as a catalyst in the coupling reaction of acid and amine in generating an active ester suitable for amidation in a waste-free catalytic manner.

Suitable solvents that may be used for the reaction include toluene, xylene, mesitylene, anisole, heptane, hexane, dimethyl formamide (DMF), dimethyl sulfoxide (DMSO), N-methyl pyrrolidone (NMP), dimethyl acetamide (DMA), N,N-diisopropyl ethylamine and ionic liquids.

The moles of catalyst may range from 0.05 to 1.5 moles with respect to 1 mole of 3-tert-butoxycarbonylamino-4-(2,4,5-trifluorophenyl)butyric acid of formula (II).

The reaction mixture is preferably heated to a reflux temperature of the solvent.

The starting materials are known and can be prepared according to processes described in the prior art.

The compound of formula (III) may be in the form of a salt. Preferably, the salt of the compound of formula (III) is the HCl salt or the HBr salt. More preferably the salt of the compound of formula (III) is the HCl salt.

When the compound of formula (III) is used in the form of a salt, the reaction is carried out in presence of a base.

The base may be selected from inorganic base or an organic base. The inorganic base may be selected from the group consisting of sodium hydroxide, potassium hydroxide, lithium hydroxide, cesium hydroxide, sodium carbonate, sodium bicarbonate, potassium carbonate, potassium bicarbonate, lithium carbonate, and cesium carbonate.

The organic base may be selected from the group consisting of N,N-diisopropyl ethylamine (Hunig's base), N,N-diisopropyl methylamine, triethyl amine, tert-butyl amine, 1-naphthyl amine, aniline, dimethyl aniline, piperidine, pyridine, imidazole, and lutidine.

The compound of formula (IV) obtained as a result of the coupling reaction of compound of formula (II) and compound of formula (III) may be deprotected in a manner known in the art to obtain sitagliptin. For instance, the deprotection of the amine group may be carried out by hydrogenation using palladium on carbon or sodium borohydride, or the deprotection of the amine group may be carried out by acid hydrolysis.

A pharmaceutically acceptable salt of sitagliptin may be prepared in situ without the isolation of intermediate compounds, wherein (R)-tert-butyl-4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV) is deprotected in situ. The deprotected compound may then be directly converted to a pharmaceutically acceptable salt of sitagliptin in situ.

Optionally, sitagliptin may be isolated, purified and then converted to a pharmaceutically acceptable salt, preferably a phosphate salt.

In an embodiment, the process of the present invention can be represented by the following reaction scheme:

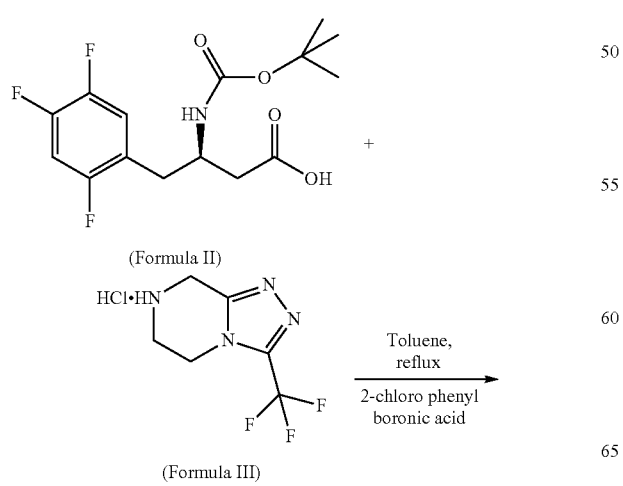

(Formula II)

(Formula III)

Toluene, reflux
2-chloro phenyl boronic acid

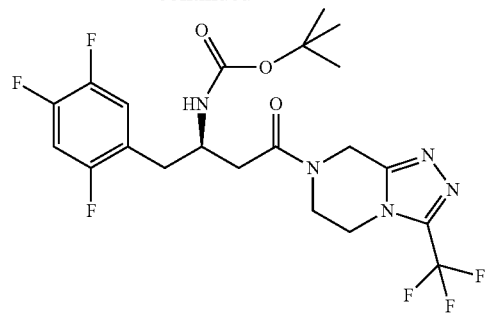

(Formula IV)

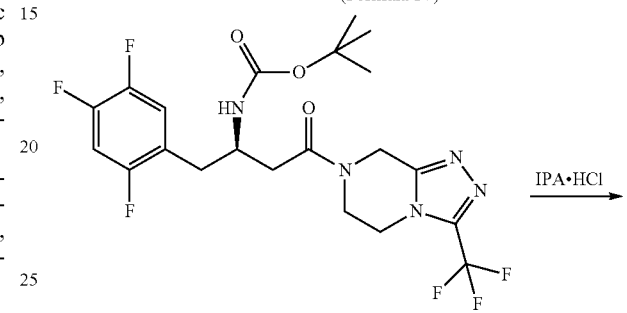

(Formula IV)

IPA·HCl

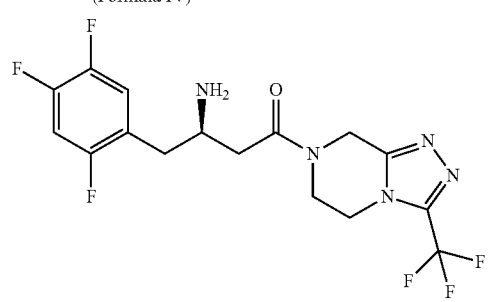

Sitagliptin

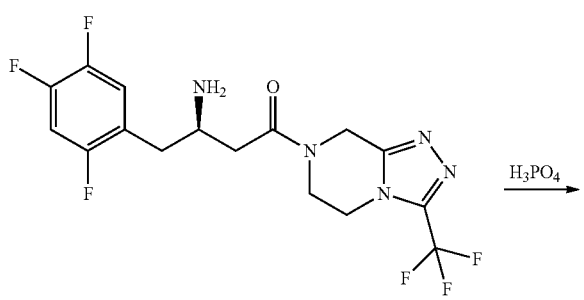

Sitagliptin

H$_3$PO$_4$

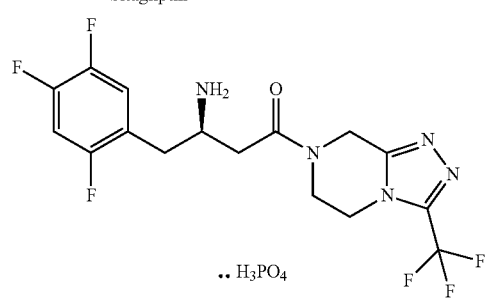

·· H$_3$PO$_4$

Sitagliptin phosphate

The details of the invention are shown in the examples which are provided below for illustration only and therefore these examples should not be construed to limit the scope of the invention.

EXAMPLES

1) Preparation of (R)-tert-butyl4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV)

25 g of 3-tert-butoxycarbonylamino-4-(2,4,5-trifluorophenyl)butyric acid of formula (II) was charged with 200 ml of toluene into a 500 ml 4 necked round bottom flask attached with dean stark apparatus, followed by the addition of 25 ml of Hunig's base at room temperature. Then 25 g of 3-(trifluoromethyl)-5,6,7,8-tetrahydro-[1,2,4]triazolo[4,3-a]pyrazine HCl was charged and stirred for 5 minutes. 11.5 g of 2-chloro phenyl boronic acid was charged to the reaction mass. After 48 hours of stirring at reflux temperature, the reaction was complete. The reaction mass was cooled to room temperature and 250 ml of water was added to it. The organic layer was separated and washed twice with 125 ml of 1N HCl. The organic layer was separated and washed with 125 ml of water followed by 6% $NaHCO_3$ and finally by 125 ml of water. The organic layer was then separated and the solvent was distilled out under vacuum. The solid obtained was stirred with 125 ml of diisopropyl ether for 2 hours, filtered and then dried under vacuum at 50° C. for 12-15 hours. HPLC was used to obtain the chromatographic purity and chiral purity.
Weight: 36.15 g (144.6% w/w, 94.98%)
Chromatographic purity: >99.0%
Chiral purity (calculated as [desired enantiomer]/[desired enantiomer+undesired enantiomer]×100): >99.5%

2) Preparation of Sitagliptin 18 g of the product obtained in example 1 was charged with 180 ml of isopropanolic HCl at 20-25° C. to obtain a clear solution and stirred for 3-4 hours. Isopropanol was distilled out under vacuum at 50° C. to obtain the residue. 130 ml of water was charged to the residue. The aqueous layer was washed with dichloromethane and cooled to 10-15° C. The pH of the aqueous layer was adjusted to 9-10 with addition of aqueous ammonia and stirred for 30 minutes at 20-25° C. and the aqueous layer was extracted with dichloromethane. All the dichloromethane layers were combined and treated with $Na_2SO_4$ followed by charcoal treatment for 25-30 minutes and then filtered through hyflo bed and the bed was washed with dichloromethane to obtain a colorless filtrate. All the filtrates were combined and concentrated under vacuum. Diisopropyl ether (80 ml) was charged and stirred at 20-25° C. for 3-4 hours. The product obtained was filtered, washed with diisopropyl ether and dried in an oven under vacuum at 50° C. for 12 hours.
HPLC was used to obtain the chromatographic purity and chiral purity.
Weight: 14.00 g (77.0% w/w, 96.88%)
Chromatographic purity: >99.0%
Chiral purity (calculated as [desired enantiomer]/[desired enantiomer+undesired enantiomer]×100): >99.5%

3) Preparation of Sitagliptin Phosphate 10 g Sitagliptin base was charged with 180 ml of isopropyl acetate, 50 ml isopropanol and 5 ml water at 20-25° C. under stirring to get a clear solution, followed by dropwise addition of a solution of 3.4 g phosphoric acid dissolved in 20 ml of isopropyl acetate over a period of 30 minutes. The reaction mixture was stirred for 5 minutes and then refluxed at 76-77° C. for 2 hours. The reaction mixture was cooled gradually to 20-25° C., stirred for 16-18 hours and then filtered, washed with isopropyl acetate and dried in oven under vacuum at 50° C. for 20-24 hours.
HPLC was used to obtain the chromatographic purity and chiral purity.
Weight: 11.78 g (117.8% w/w, 94.92%)
Chromatographic purity: 99.9%
Chiral purity (calculated as [desired enantiomer]/[desired enantiomer+undesired enantiomer]×100): >99.5%

4) Preparation of Sitagliptin Phosphate 10 g of 3-tert-butoxycarbonylamino-4-(2,4,5-trifluorophenyl)butyric acid of formula (II) was charged with 100 ml of toluene into a 500 ml 4 necked round bottom flask attached with dean stark apparatus followed by addition of 10 ml Hunigs base at room temperature. 10 g of 3-(trifluoromethyl)-5,6,7,8-tetrahydro-[1,2,4]triazolo[4,3-a]pyrazine HCl was then charged and after stirring for 5 minutes, 4.69 g of 2-chloro phenyl boronic acid was charged. The reaction mass was heated to reflux and maintained till completion of the reaction. After completion of the reaction, the reaction mass was cooled to room temperature and 100 ml of water was added to it. The organic layer was separated and washed twice with 50 ml of 1N HCl. The separated organic layer was washed with 50 ml of water followed by 6% $NaHCO_3$ and finally by 50 ml of water. The organic layer was collected and the solvent was distilled out under vacuum. The residue obtained was stirred with 100 ml of isopropanolic HCl for 3 hours and then concentrated under vacuum to get residue again. 100 ml of water was charged to the residue and the aqueous layer was washed with 4×50 ml dichloromethane and cooled to 10-15° C. and the pH of the aqueous layer was adjusted to 9-10 with dropwise addition of aqueous ammonia. The reaction mass was stirred for 30 minutes at 20-25° C. and the aqueous layer was extracted with dichloromethane. All the dichloromethane layers were combined and treated with $Na_2SO_4$ followed by charcoal treatment for 25-30 minutes and filtered through hyflo bed and washed with dichloromethane to obtain colorless filtrate. All the filtrates were combined and concentrated under vacuum to get oil. To this oil 130 ml of isopropyl acetate, 40 ml of isopropanol and 4 ml of water were charged at 20-25° C. under stirring to get the clear solution, followed by dropwise addition of a solution of 2.56 g phosphoric acid dissolved in 20 ml of isopropyl acetate over a period of 30 minutes. The reaction mass was stirred for 5 minutes and then refluxed at 76-77° C. for 2 hours. The reaction mass was then cooled gradually to 20-25° C. and stirred for 16-18 hours. The solid obtained was filtered, washed with isopropyl acetate and dried the material in oven under vacuum at 50° C. for 20-24 hours.
HPLC was used to obtain the chromatographic purity and chiral purity.
Weight: 13.7 g. (137.0% w/w, 90.31%)
Chromatographic purity: 99.9%
Chiral purity (calculated as [desired enantiomer]/[desired enantiomer+undesired enantiomer]×100): >99.5%

5) Preparation of (R)-tert-butyl4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV)

5 g of 3-tert-butoxycarbonylamino-4-(2,4,5-trifluorophenyl)butyric acid of formula (II) was charged with 40 ml of xylene into a 500 ml 4 necked round bottom flask attached with dean stark apparatus followed by 5 ml of Hunig's base at room temperature. Then 5 g of 3-(trifluoromethyl)-5,6,7,8-tetrahydro-[1,2,4]triazolo[4,3-a]pyrazine HCl was charged and stirred for 5 minutes. 2.34 g of 3-chloro phenyl boronic acid was charged to the reaction mass. After 48 hours of stirring at reflux temperature, the reaction was complete. The reaction mass was cooled to room temperature and 50 ml of water was added to it. The organic layer was separated and washed twice with 25 ml of 1N HCl. The organic layer was separated and washed with 25 ml of water followed by 6% $NaHCO_3$ and finally by 25 ml of water. The organic layer was then separated, treated with sodium sulfate and then with charcoal and filtered. The solvent was distilled out under vacuum. The solid obtained was stirred with 25 ml of diisopropyl ether for 2 hours, filtered, washed with diisopropyl ether and then dried under vacuum at 50° C. for 12-15 hours.

HPLC was used to obtain the chromatographic purity and chiral purity.
Weight: 6.0 g (120% w/w, 78.84%)
Chromatographic purity: >88.0%
Chiral purity (calculated as [desired enantiomer]/[desired enantiomer+undesired enantiomer]×100): >98.5%

6) Preparation of (R)-tert-butyl4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV)

5 g of 3-tert-butoxycarbonylamino-4-(2,4,5-trifluorophenyl)butyric acid of formula (II) was charged with 40 ml of toluene into a 500 ml 4 necked round bottom flask attached with dean stark apparatus followed by 5 ml of Hunig's base at room temperature. Then 5 g of 3-(trifluoromethyl)-5,6,7,8-tetrahydro-[1,2,4]triazolo[4,3-a]pyrazine HCl was charged and stirred for 5 minutes. 2.34 g of 4-chloro phenyl boronic acid was charged to the reaction mass. After 48 hours of stirring at reflux temperature, the reaction was complete. The reaction mass was cooled to room temperature and 50 ml of water was added to it. The organic layer was separated and washed twice with 25 ml of 1N HCl. The organic layer was separated and washed with 25 ml of water followed by 6% $NaHCO_3$ and finally by 25 ml of water. The organic layer was then separated, treated with sodium sulfate and then with charcoal and filtered. The solvent was distilled out under vacuum. The solid obtained was stirred with 25 ml of diisopropyl ether for 2 hours, filtered, washed with diisopropyl ether and then dried under vacuum at 50° C. for 12-15 hours.

HPLC was used to obtain the chromatographic purity and chiral purity.
Weight: 6.5 g (130% w/w, 85.41%)
Chromatographic purity: >87.0%
Chiral purity (calculated as [desired enantiomer]/[desired enantiomer+undesired enantiomer]×100): >98.5%

7) Preparation of (R)-tert-butyl4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV)

100 g of 3-tert-butoxycarbonylamino-4-(2,4,5-trifluorophenyl)butyric acid of formula (II) was charged with 800 ml of toluene into a 2 liter 4 necked round bottom flask attached with dean stark apparatus followed by 70 ml of triethyl amine at room temperature. Then 100 g of 3-(trifluoromethyl)-5,6,7,8-tetrahydro-[1,2,4]triazolo[4,3-a]pyrazine HCl was charged and stirred for 5 minutes. 7.5 g of phenyl boronic acid was charged to the reaction mass. After 48 hours of stirring at reflux temperature, the reaction was complete. The reaction mass was cooled to room temperature and 1000 ml of water was added to it. The organic layer was separated and washed twice with 500 ml of 1N HCl. The organic layer was separated and washed with 500 ml of water followed by 6% $NaHCO_3$ and finally by 500 ml of water. The organic layer was then separated, treated with sodium sulfate and then with charcoal and filtered. The solvent was distilled out under vacuum. The solid obtained was stirred with 500 ml of diisopropyl ether for 2 hours, filtered, washed with diisopropyl ether and then dried under vacuum at 50° C. for 12-15 hours.

HPLC was used to obtain the chromatographic purity and chiral purity.
Weight: 140 g (140.0% w/w, 91.95%)
Chromatographic purity: >98.0%
Chiral purity (calculated as [desired enantiomer]/[desired enantiomer+undesired enantiomer]×100): >99.5%

The present invention has been described above purely by way of example. It should be noted that modifications in detail may be made within the scope of the appended claims.

The invention claimed is:

1. A process for the preparation of a compound of formula (IV)

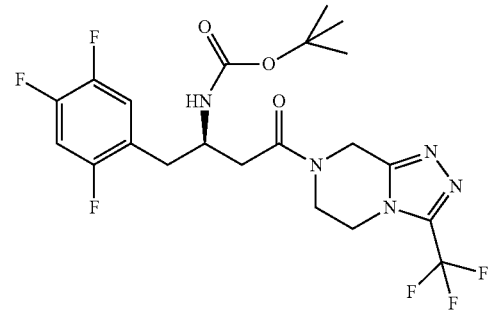

Formula (IV)

which process comprises:
a) condensing 3-tert-butoxycarbonylamino-4-(2,4,5-trifluorophenyl)butyric acid of formula (II)

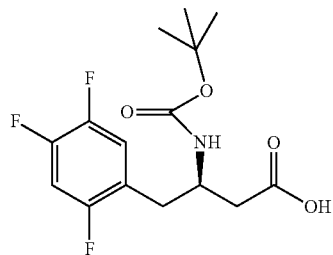

Formula (II)

with 3-(trifluoromethyl)-5,6,7,8-tetrahydro-[1,2,4]triazolo[4,3-a]pyrazine of formula (III) or a salt thereof

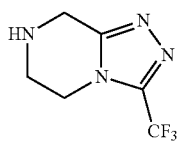

Formula (III)

in presence of a catalyst to obtain (R)-tert-butyl-4-oxo-4-(3-(trifluoromethyl)-5,6-dihydro-[1,2,4]-triazolo[4,3-a]pyrazin-7(8H)-yl)-1-(2,4,5-trifluorophenyl)butan-2-yl-carbamate of formula (IV) or a pharmaceutically acceptable salt thereof;

wherein the catalyst is represented by the compound of formula (V)

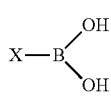

(V)

wherein X is independently selected from hydroxy, straight chain or branched $C_{1-5}$ alkyl optionally substituted with one or more groups, non-aromatic or aromatic $C_{6-13}$ aryl optionally substituted with one or more groups, and an optionally substituted heterocyclic ring having one to four heteroatoms selected from oxygen, sulfur and nitrogen.

2. A process according to claim 1 wherein X is an aryl group and the aryl group is phenyl.

3. A process according to claim 1 wherein X is an aryl group that is substituted by one or more substituents selected from the group consisting of halogen, nitro, $C_{1-9}$ alkyl, $C_{1-9}$ alkenyl, and $C_{1-9}$ alkoxy.

4. A process according to claim 1 wherein X is a heterocyclic ring substituted with one or more substituents selected from the group consisting of halogen, nitro, $C_{1-9}$ alkyl, $C_{1-9}$ alkenyl, and $C_{1-9}$ alkoxy.

5. A process according to claim 1, further comprising:
b) deprotecting the compound of formula (IV) or its pharmaceutically acceptable salt obtained in step a) to obtain a compound of formula (I)

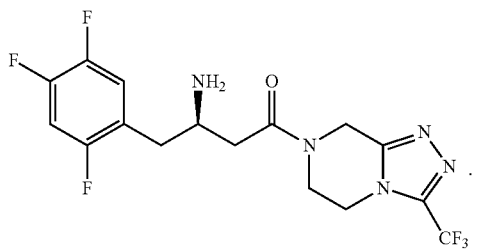

(I)

6. A process according to claim 5 wherein the deprotection is by hydrogenation or acid hydrolysis.

7. A process according to claim 5 wherein the deprotection is by hydrogenation using palladium on carbon or sodium borohydride.

8. A process according to claim 5 wherein compound of formula (IV) is isolated prior to the deprotection step (b).

9. A process according to claim 5 wherein compound of formula (IV) is deprotected to obtain compound of formula (I) in situ without isolation of compound of formula (IV).

10. A process according to claim 5 further comprising converting the compound of formula (I) obtained in step b) to a pharmaceutically acceptable salt.

11. A process according to claim 10 wherein the compound of formula (I) is isolated and purified prior being converted to a pharmaceutically acceptable salt.

12. A process according to claim 10 wherein the compound of formula (I) is converted to a pharmaceutically acceptable salt in situ.

13. A process according to claim 9 wherein the pharmaceutically acceptable salt is the phosphate salt.

14. A process according to claim 1 wherein the catalyst is selected from the group consisting of phenyl boronic acid, 2-halophenyl boronic acid, 3-halophenylboronic acid, and 4-halophenylboronic acid.

15. A process according to claim 1 wherein the catalyst is selected from the group consisting of 2-chlorophenyl boronic acid, 3-chlorophenyl boronic acid, 4-chlorophenyl boronic acid, 2-bromophenyl boronic acid, 3-bromophenyl boronic acid, and 4-bromophenyl boronic acid.

16. A process according to claim 1 wherein the catalyst is phenyl boronic acid.

17. A process according to claim 1 wherein the amount of catalyst used is in the range of from 0.05 to 1.5 moles with respect to 1 mole of 3-tert-butoxycarbonylamino-4-(2,4,5-trifluorophenyl) butyric acid of formula (II).

18. A process according to claim 1 wherein the solvent used for the reaction is selected from the group consisting of toluene, xylene, mesitylene, anisole, heptane, hexane, dimethyl formamide (DMF), dimethyl sulfoxide (DMSO), N-methyl pyrrolidone (NMP), dimethyl acetamide (DMA), N,N-diisopropyl ethylamine and ionic liquids.

19. A process according to claim 1 wherein 3-(trifluoromethyl)-5,6,7,8-tetrahydro-[1,2,4]triazolo[4,3-a]pyrazine of formula (III) is in the form of a salt.

20. A process according to claim 19 wherein 3-(trifluoromethyl)-5,6,7,8-tetrahydro-[1,2,4]triazolo[4,3-a]pyrazine of formula (III) is in the form of the hydrobromide salt or the hydrochloride salt.

21. A process according to claim 19 wherein the reaction is carried out in presence of a base.

22. A process according to claim 21 wherein the base is selected from an inorganic base or an organic base.

23. A process according to claim 22 wherein the base is an inorganic base selected from the group consisting of sodium hydroxide, potassium hydroxide, lithium hydroxide, cesium hydroxide, sodium carbonate, sodium bicarbonate, potassium carbonate, potassium bicarbonate, lithium carbonate, and cesium carbonate.

24. A process according to claim 22 wherein the base is an organic base selected from the group consisting of N,N-diisopropyl ethylamine, N,N-diisopropyl methylamine, triethyl amine, tert-butyl amine, 1-naphthyl amine, aniline, dimethyl aniline, piperidine, pyridine, imidazole, and lutidine.

25. A process according to claim 22 wherein the base is N,N-diisopropyl ethylamine or triethyl amine.

* * * * *